(12) United States Patent
Adams

(10) Patent No.: US 8,021,338 B2
(45) Date of Patent: Sep. 20, 2011

(54) PERCUTANEOUS ENDOSCOPIC JEJUNOSTOMY ACCESS NEEDLE

(75) Inventor: Mark L. Adams, Sandy, UT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 732 days.

(21) Appl. No.: 11/226,547

(22) Filed: Sep. 14, 2005

(65) Prior Publication Data

US 2007/0060889 A1    Mar. 15, 2007

(51) Int. Cl.
*A61M 5/178* (2006.01)

(52) U.S. Cl. ......... 604/164.07; 604/164.01; 604/164.09; 604/164.11

(58) Field of Classification Search ............. 604/164.01, 604/164.06, 164.07, 164.08, 164.09, 164.11, 604/170.01, 170.02, 165.01, 165.02, 165.04
See application file for complete search history.

(56) References Cited

U.S. PATENT DOCUMENTS

| | | |
|---|---|---|
| 1,248,492 A | 12/1917 | Hill |
| 3,225,762 A | 12/1965 | Guttman |
| 3,536,073 A | 10/1970 | Farb |
| 3,993,079 A | 11/1976 | Henriques de Gatztanondo |
| 4,230,123 A | 10/1980 | Hawkins, Jr. |
| 4,269,186 A | 5/1981 | Loveless et al. |
| 4,500,312 A | 2/1985 | McFarlane |
| 4,762,516 A | 8/1988 | Luther et al. |
| 4,781,692 A | 11/1988 | Jagger et al. |
| 4,828,547 A | 5/1989 | Sahi et al. |
| 4,832,696 A | 5/1989 | Luther et al. |
| 4,861,334 A | 8/1989 | Nawaz |
| 4,900,306 A | 2/1990 | Quinn et al. |
| 4,950,252 A | 8/1990 | Luther et al. |
| 5,009,642 A | 4/1991 | Sahi |
| 5,112,310 A | 5/1992 | Grobe |

(Continued)

FOREIGN PATENT DOCUMENTS

DE    8915299 U1    2/1990

(Continued)

OTHER PUBLICATIONS

International Search Report dated Jan. 23, 2007, from PCT Appln. No. PCT/US2006/035891.

*Primary Examiner* — Theodore Stigell
*Assistant Examiner* — Laura Schell
(74) *Attorney, Agent, or Firm* — Kenyon & Kenyon LLP

(57) ABSTRACT

An access needle suitable for use in percutaneous endoscopic jejunostomy procedures. In one embodiment, the access needle includes a stylet assembly, a safety sheath assembly and a cannula assembly. The stylet assembly includes a stylet and a stylet hub. The stylet has a proximal end and a sharpened distal end, the proximal end of the stylet being mounted within the stylet hub. The safety shield assembly includes a sheath and a shuttle. The sheath, which has a blunt distal end, coaxially surrounds the stylet. The proximal end of the sheath is fixed to the shuttle, the shuttle being movable between a first position in which the sharpened distal end of the stylet is exposed and a second position in which the sharpened distal end of the stylet is shielded by the blunt distal end of the sheath. The cannula assembly includes a cannula and a cannula hub, the cannula hub being fixed to the proximal end of the cannula. The cannula hub is detachably engageable with the shuttle to move the shuttle between its first and second positions.

19 Claims, 9 Drawing Sheets

U.S. PATENT DOCUMENTS

| | | | |
|---|---|---|---|
| 5,114,407 A * | 5/1992 | Burbank | 604/164.12 |
| 5,167,627 A | 12/1992 | Clegg et al. | |
| 5,306,259 A | 4/1994 | Fischell et al. | |
| 5,312,345 A | 5/1994 | Cole | |
| 5,312,354 A * | 5/1994 | Allen et al. | 604/157 |
| 5,318,543 A | 6/1994 | Ross et al. | |
| 5,380,292 A | 1/1995 | Wilson | |
| 5,391,159 A | 2/1995 | Hirsch et al. | |
| 5,531,678 A | 7/1996 | Tomba et al. | |
| 5,540,662 A | 7/1996 | Nicholson | |
| 5,667,514 A * | 9/1997 | Heller | 606/108 |
| 5,672,158 A | 9/1997 | Okada et al. | |
| 5,743,882 A | 4/1998 | Luther | |
| 5,851,195 A | 12/1998 | Gill | |
| 5,858,002 A | 1/1999 | Jesch | |
| 5,951,520 A | 9/1999 | Burzynski et al. | |
| 5,984,941 A | 11/1999 | Wilson et al. | |
| 6,030,364 A | 2/2000 | Durgin et al. | |
| D424,194 S | 5/2000 | Holdaway et al. | |
| 6,090,073 A | 7/2000 | Gill | |
| 6,254,574 B1 | 7/2001 | Burzynski et al. | |
| 6,319,266 B1 | 11/2001 | Stellon et al. | |
| 6,391,007 B2 | 5/2002 | Chang et al. | |
| 6,475,189 B1 | 11/2002 | Lilley, Jr. | |
| 6,524,277 B1 | 2/2003 | Chang | |
| 6,673,058 B2 | 1/2004 | Snow | |
| 6,689,142 B1 | 2/2004 | Tremaglio, Jr. et al. | |
| 6,808,519 B2 | 10/2004 | Fanelli et al. | |
| 6,910,581 B2 | 6/2005 | McMichael et al. | |
| 7,001,396 B2 * | 2/2006 | Glazier et al. | 606/108 |
| 2001/0018572 A1 | 8/2001 | Kinsey et al. | |
| 2002/0072711 A1 | 6/2002 | Cindrich | |
| 2002/0095123 A1 | 7/2002 | Smutney et al. | |
| 2003/0088212 A1 * | 5/2003 | Tal | 604/163 |
| 2003/0171718 A1 * | 9/2003 | DeLegge et al. | 604/164.01 |
| 2004/0092879 A1 * | 5/2004 | Kraus et al. | 604/158 |

FOREIGN PATENT DOCUMENTS

| | | |
|---|---|---|
| DE | 40 38 952 A1 | 6/1992 |
| EP | 0 583 049 A1 | 2/1994 |
| WO | WO 94/27524 A1 | 12/1994 |
| WO | WO 00/23131 | 4/2000 |

* cited by examiner

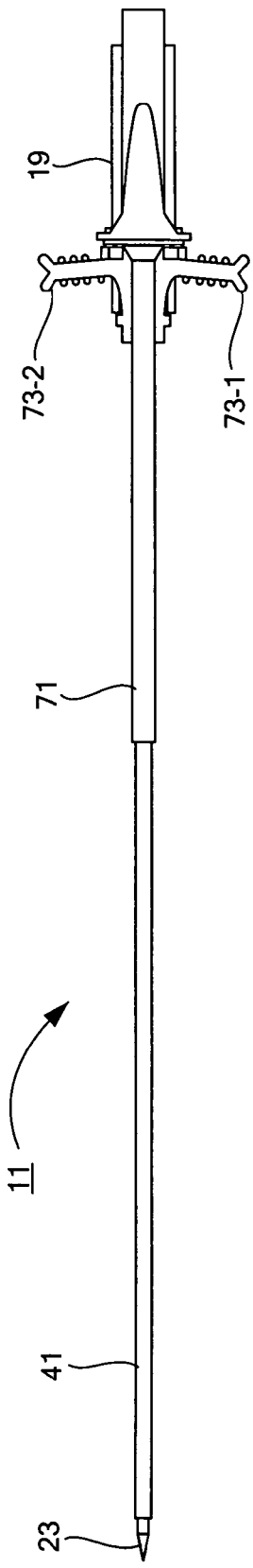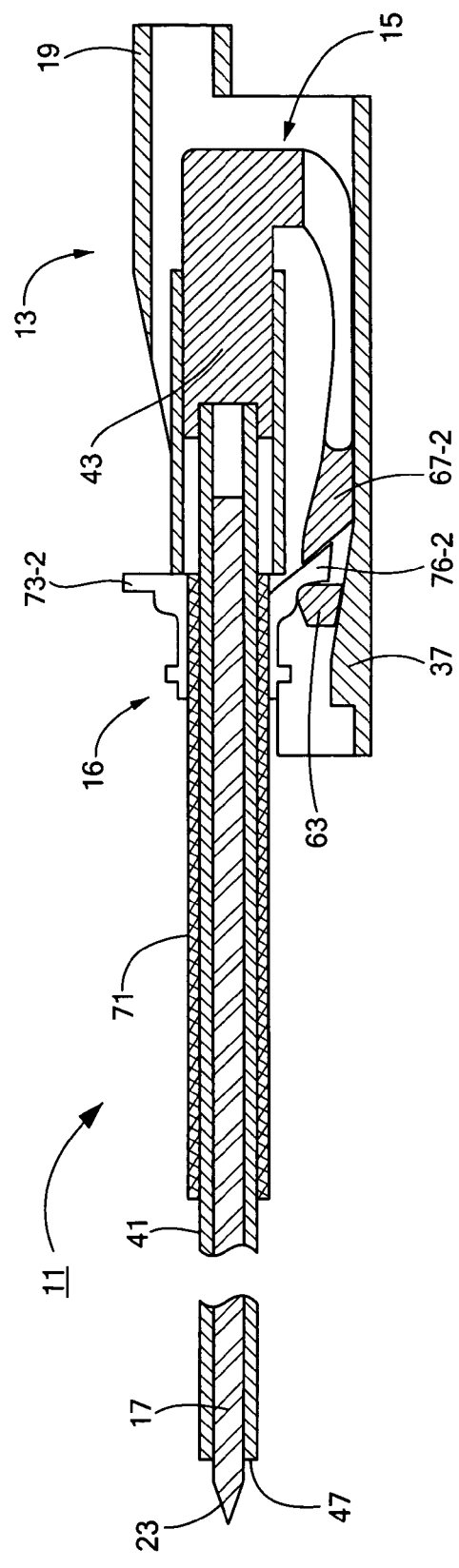

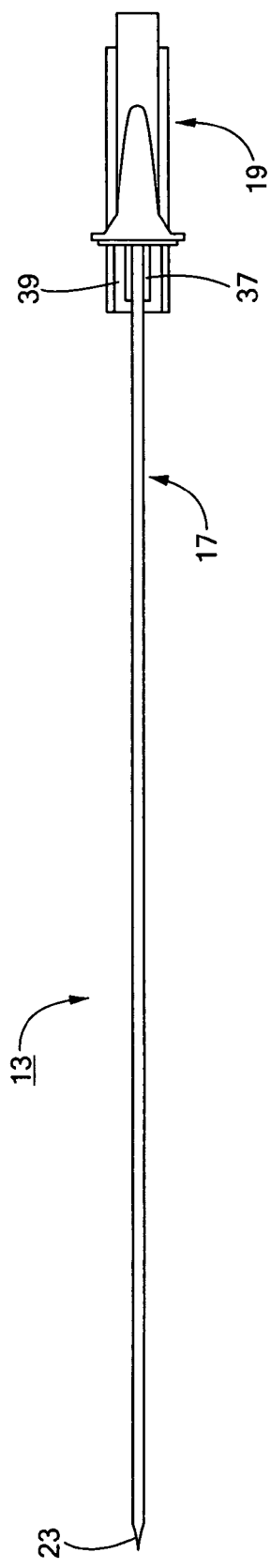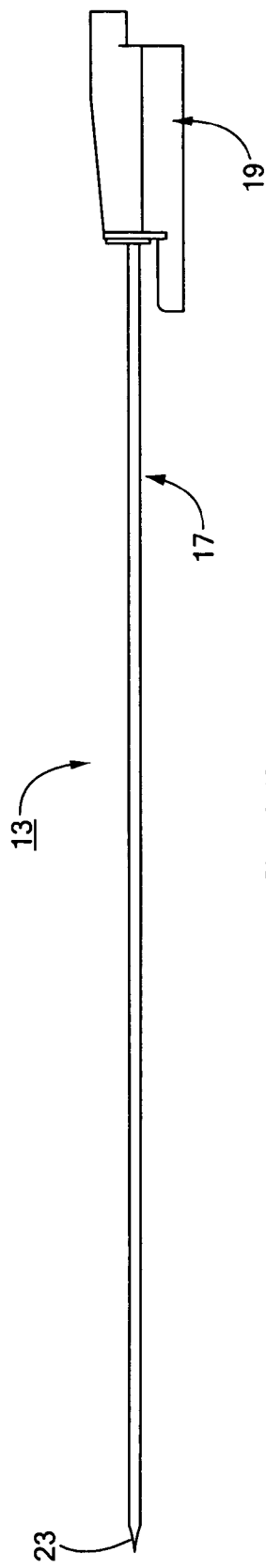
FIG. 4(a)
FIG. 4(b)

FIG. 5(a)
FIG. 5(b)

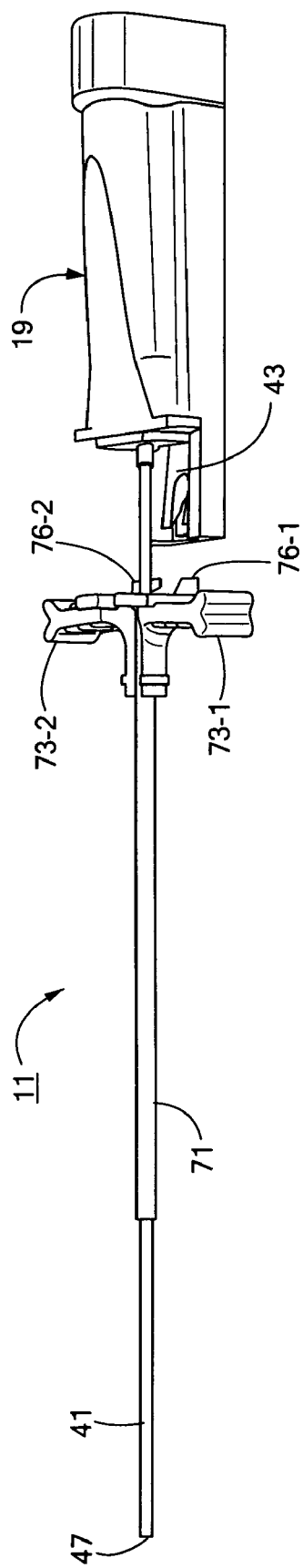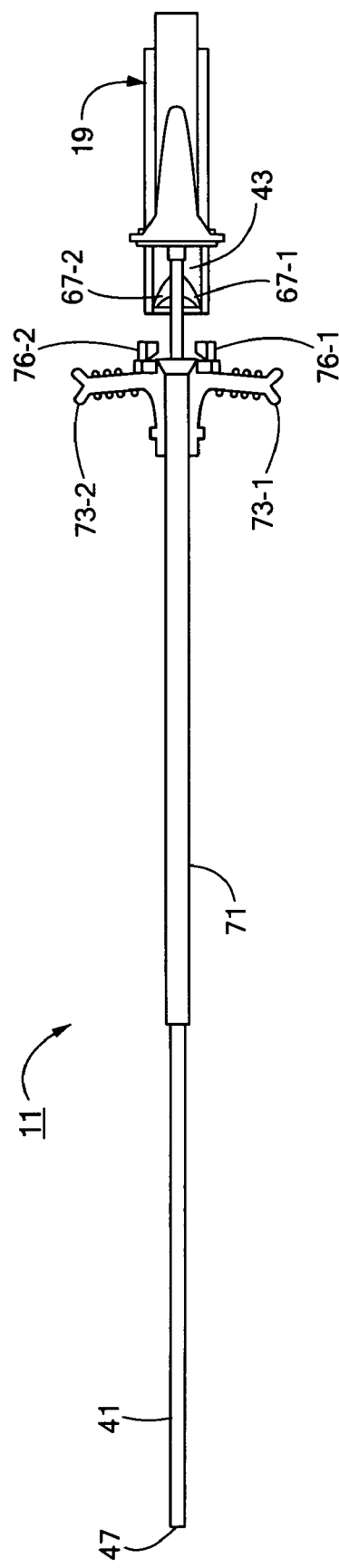
FIG. 8(a)
FIG. 8(b)

PERCUTANEOUS ENDOSCOPIC JEJUNOSTOMY ACCESS NEEDLE

BACKGROUND OF THE INVENTION

The present invention relates generally to access needles suitable for use in percutaneous endoscopic gastrostomy (PEG) procedures and percutaneous endoscopic jejunostomy (PEJ) procedures and relates more particularly to a novel access needle particularly well-suited for use in PEJ procedures.

Certain patients are unable to take food and/or medications transorally due to an inability to swallow. Such an inability to swallow may be due to a variety of reasons, such as esophageal cancer, neurological impairment and the like. Although the intravenous administration of food and/or medications to such patients may be a viable short-term approach, it is not well-suited for the long term. Accordingly, the most common approach to the long-term feeding of such patients involves gastrostomy, i.e., the creation of a feeding tract or stoma between the stomach and the upper abdominal wall. Feeding is then typically performed by administering food through a catheter or feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy and result in the implantation of a gastrostomy feeding tube assembly (also referred to as a percutaneous endoscopic gastrostomy (PEG) device) in the patient. Two of the more common techniques for implanting a PEG device in a patient are "the push method" (also known as "the Sacks-Vine method") and "the pull method" (also known as "the Gauderer-Ponsky method"). Information regarding the foregoing two methods may be found in the following patents, all of which are incorporated herein by reference: U.S. Pat. No. 5,391,159, inventors Hirsch et al., which issued Feb. 21, 1995; U.S. Pat. No. 5,167,627, inventors Clegg et al., which issued Dec. 1, 1992; U.S. Pat. No. 5,112,310, inventor Grobe, which issued May 12, 1992; U.S. Pat. No. 4,900,306, inventors Quinn et al., which issued Feb. 13, 1990; and U.S. Pat. No. 4,861,334, inventor Nawaz, which issued Aug. 29, 1989.

According to "the push method," the distal end of an endoscope is inserted into a patient's mouth and is passed through the esophagus into the stomach. After distension of the stomach by inflation with air, an entry site on the abdomen is identified using the endoscope for transillumination, and an incision is made by passing the sharpened tip of a needle surrounded by a cannula (the combination of the needle and the cannula also referred to in the art as an "access needle") through the abdominal wall and into the stomach. A snare is inserted into the stomach via the endoscope and is looped over the inserted end of the needle portion of the access needle. The snare is then "walked" up the needle until the cannula portion of the access needle is snared. The snared cannula is then pulled externally to tack the cannula to the stomach and, in turn, to secure the stomach wall to the abdominal wall. The needle portion of the access needle is then removed from the patient while keeping the cannula portion of the access needle in place. A first end of a flexible guidewire (also known in the art as a "pushwire") is then passed through the cannula and into the stomach where it is grasped by the snare, the second end of the guidewire remaining external to the patient. The endoscope and the snare are then withdrawn from the mouth of the patient to deliver the first end of the guidewire.

A push-type catheter implanting assembly is then inserted over the first end of the guidewire and is pushed over the guidewire towards its second end. The push-type catheter implanting assembly typically comprises a gastrostomy feeding tube, the gastrostomy feeding tube having a dome-shaped internal bolster disposed at its trailing end and having a tubular dilator serially connected to its leading end. The gastrostomy feeding tube and the internal bolster are typically made of a soft, biocompatible material, like silicone rubber, and typically form a unitary structure. The dilator, which tapers in outer diameter from its trailing end to its leading end, is typically made of polyethylene or a like material which is stiffer than silicone but which still possesses some flexibility. Advancement of the push-type catheter implanting assembly over the guidewire continues until the front end of the dilator reaches the cannula and pushes the cannula out through the abdominal wall of the patient. The front end of the dilator is then pulled through the abdominal wall until the front end of the gastrostomy feeding tube emerges from the abdomen and, thereafter, the internal bolster at the rear end of the gastrostomy feeding tube engages the stomach wall. The guidewire is then removed from the patient. The clinician then re-intubates the patient with the endoscope and uses an optical channel in the endoscope to inspect whether the internal bolster is properly seated in the stomach.

If the internal bolster is properly placed against the stomach wall, a length of the externally-extending portion of the implanted gastrostomy feeding tube is then typically cut and removed from the implanted tube to reduce the externally-extending portion of the tube to a desired length (typically about 4-6 inches). (The removal of the leading end of the gastrostomy feeding tube also results in the removal of the dilator, which is connected thereto.) An external bolster is typically secured to the remaining externally-extending portion of the feeding tube to engage the abdomen in such a way as to prevent longitudinal movement of the feeding tube into the stomach. Additionally, a "Y-port" adapter is typically attached to the external end of the feeding tube, the Y-port adapter being adapted to receive a pair of connector tips through which food and/or medications may be dispensed. In addition, a detachable locking clip is typically secured to the implanted feeding tube at a point between the external bolster and the Y-port adapter to prevent gastric fluids from escaping through the proximal end of the feeding tube when the feeding tube is not in use.

The "pull method" is similar in some respects to the above-described "push method," the pull method differing from the push method in that, after the cannula is snared and the needle is removed from its cannula, a looped first end of a suture (also known in the art as a "pullwire") is inserted through the cannula and into the stomach where it is grasped by the snare, the second end of the suture remaining external to the patient. The endoscope and the snare are then withdrawn from the mouth of the patient to deliver the first end of the suture. The first end of the suture is then coupled to the leading end of a pull-type catheter implanting assembly, the pull-type catheter implanting assembly typically comprising a gastrostomy feeding tube having an internal bolster integrally formed at its trailing end and a plastic fitting attached to its leading end. The plastic fitting typically has a barbed rear portion mounted within the leading end of the feeding tube and a conical front portion that serves as a dilator, said conical front portion tapering in diameter from the leading end of the feeding tube to a front tip. A wire loop is fixed to the front tip of the plastic fitting, the first end of the suture being tied to the wire loop. Using the second end of the suture, the pull-type catheter implanting assembly is then pulled retrograde through the patient until the gastrostomy feeding tube emerges from the abdomen of the patient and the internal bolster engages the stomach wall of the patient. Next, as is the case in the push method, the clinician then re-intubates the patient with the endoscope in order to visually inspect the placement of the internal bolster within the stomach. If the bolster is properly seated in the stomach, the externally-extending portion of the implanted gastrostomy feeding tube is then typically cut to a desired length and one or more of an external bolster, a Y-port and a clamp are attached to the feeding tube.

Access needles of the type that are typically used in percutaneous endoscopic gastrostomies have their genesis in radiology and cardiology and typically come in two different varieties. One such access needle is referred to in the art as a Seldinger needle and comprises a solid metal needle (or stylet) removably mounted within a metal cannula. A plastic needle hub is fixed to the proximal end of the metal needle, and a plastic cannula hub is fixed to the proximal end of the metal cannula. The needle hub and the cannula hub are sized and shaped to permit a portion of the needle hub to be removably inserted into the cannula hub in such a way as to delimit insertion of the needle through the cannula. A tab is provided on the needle hub and a corresponding slot is provided on the cannula hub, said slot being adapted to receive said tab in order to permit said needle and said cannula to be placed in a particular rotational orientation relative to one another. The cannula hub is also shaped to include a lateral flange upon which a user may rest, for example, his forefinger and middle finger.

The other type of access needle commonly used to perform percutaneous endoscopic gastrostomies is an ANGIO-CATH® access needle, which comprises a hollow metal needle removably mounted within a plastic cannula. A plastic needle hub is fixed to the proximal end of the metal needle, and a plastic cannula hub is fixed to the proximal end of the plastic cannula. The needle hub and the cannula hub are sized and shaped to permit a portion of the needle hub to be removably inserted into the cannula hub in such a way as to delimit insertion of the needle through the cannula. No means is provided in an ANGIOCATH® access needle for fixing the rotational orientation of the needle relative to the cannula when the needle hub is inserted into the cannula hub.

In both a Seldinger needle and an ANGIOCATH® needle, the lengths of the needle and the cannula are such that, with the needle fully inserted into the cannula, only the needle tip extends distally beyond the distal end of the cannula. Seldinger needles typically have a smaller diameter than do ANGIOCATH® needles (20 gauge needle and 18 gauge cannula vs. 16 gauge needle and 14 gauge cannula, respectively); however, more doctors have been trained using ANGIO-CATH® needles and, therefore, are more comfortable with and use ANGIOCATH® needles.

Although gastrostomies are the most common approach to the long-term feeding of patients unable to swallow, there are situations in which it is desirable to provide food directly into a patient's jejunum without passing through the patient's stomach. This has typically been accomplished by using techniques similar to those described above, except that the internal end of a feeding tube is implanted in the patient's jejunum, instead of the patient's stomach. One difficulty, however, that has been encountered in implanting feeding tubes into the jejunum has been in the piercing of the jejunum by the access needle so as to create an insertion hole through which a guide wire or suture may be inserted. This difficulty arises, in part, because the jejunum is narrow and thus hard to locate externally and, in part, because the jejunum is not fixed within the body at any particular location. As a result, not only is it difficult to actually pierce the jejunum with an access needle (the access needle frequently missing the jejunum or just pushing the jejunum aside without penetrating it), but even if the jejunum is actually pierced by the access needle, subsequent movement of the jejunum may cause the access needle to become dislodged therefrom. Consequently, it is generally desirable to use as small a diameter needle as possible to pierce the jejunum. This maximizes the chance that the jejunum, if struck by the access needle, will be pierced thereby and also minimizes the size of the insertion hole (which is desirable for obvious reasons).

One approach that has recently been devised to address the above-identified problems with piercing the jejunum involves piercing the jejunum with a small diameter needle, grabbing the distal end of the needle with an endoscopically-placed snare, using said small diameter needle (with the snare secured thereto) to anchor the jejunum against the abdominal wall, piercing the thus-anchored jejunum with an access needle at a site proximate to the first piercing site, transferring the snare from the small diameter needle to the cannula of the access needle, removing the small diameter needle from the jejunum, and then proceeding in the conventional fashion by removing the needle of the access needle from its cannula, inserting a guide wire or suture into the cannula for grabbing by the snare, etc.

Another approach to piercing the jejunum is disclosed in presently-pending and commonly-assigned U.S. patent application Ser. No. 10/300,702, inventors Rebecca DeLegge et al., filed Nov. 20, 2002, and incorporated herein by reference.

SUMMARY OF THE INVENTION

It is an object of the present invention to provide a novel access needle.

It is another object of the present invention to provide an access needle that is particularly well-suited for use in percutaneous endoscopic jejunostomy (PEJ) procedures.

Therefore, according to one aspect of the invention, there is provided an access needle, said access needle comprising (a) a stylet, said stylet having a proximal end and a sharpened distal end; (b) a sheath coaxially surrounding said stylet, said sheath having a proximal end a blunt distal end; (c) a shuttle, said shuttle being coupled to said proximal end of said sheath, said shuttle being movable between a first position in which said sharpened distal end of said stylet is exposed and a second position in which said sharpened distal end of said stylet is shielded by said blunt distal end of said sheath; and (d) a cannula, said cannula having a proximal end and a distal end, said sheath being removably coaxially received in said cannula.

According to another aspect of the invention, there is provided an access needle comprising (a) a stylet assembly, said stylet assembly comprising a stylet and a stylet hub, said stylet having a proximal end and a sharpened distal end, said proximal end being fixedly mounted within said stylet hub; (b) a safety sheath assembly, said safety sheath assembly comprising a sheath and a shuttle, said sheath coaxially receiving said stylet and having a proximal end and a blunt distal end, said shuttle having a complete range of motion between a forwardmost position in which said sharpened distal end of said stylet is exposed and a rearwardmost position in which said sharpened distal end of said stylet is shielded by said blunt distal end of said sheath; and (c) a cannula, said cannula having a proximal end a distal end, said sheath being removably coaxially received in said cannula.

Additional objects, as well as aspects, features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 2 is a top view of the access needle of FIG. 1, with the stylet of the access needle shown in an exposed state;

FIG. 3 is a section view of the access needle of FIG. 1, with the stylet of the access needle shown in an exposed state;

FIGS. 4(a) through 4(d) are top, side, front and section views, respectively, of the stylet assembly of the access needle of FIG. 1;

FIGS. 5(a) and 5(b) are top and side views, respectively, of the safety sheath assembly of the access needle of FIG. 1;

FIGS. 8(a) and 8(b) are perspective and top view, respectively, of the access needle of FIG. 1, with the cannula assembly moved sufficiently distally so that the cannula assembly is disengaged from the shuttle.

DETAILED DESCRIPTION OF PREFERRED EMBODIMENTS

Figure 1:
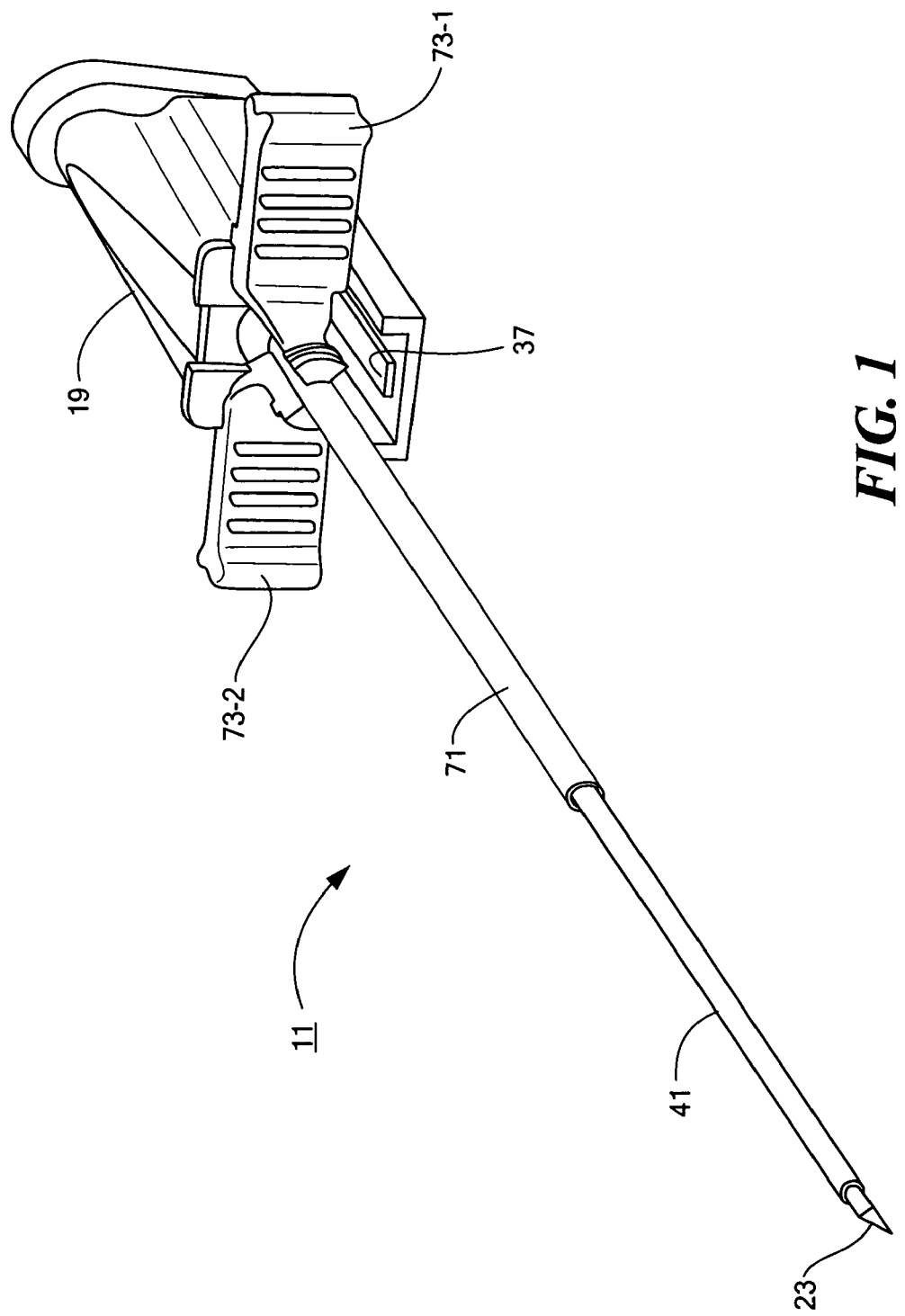
FIG. 1 is a perspective view of one embodiment of an access needle constructed according to the teachings of the present embodiment, with the stylet of the access needle shown in an exposed state.
Figure 4C:
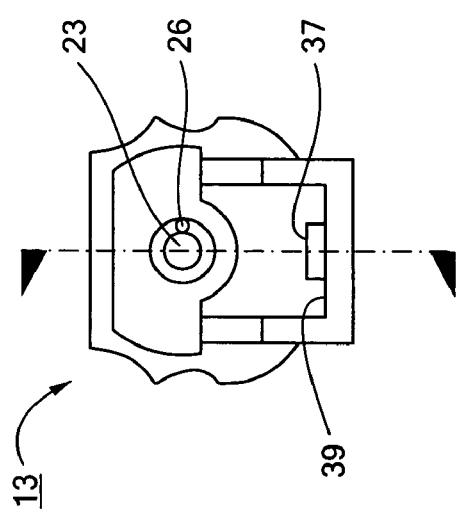
Figure 4D:
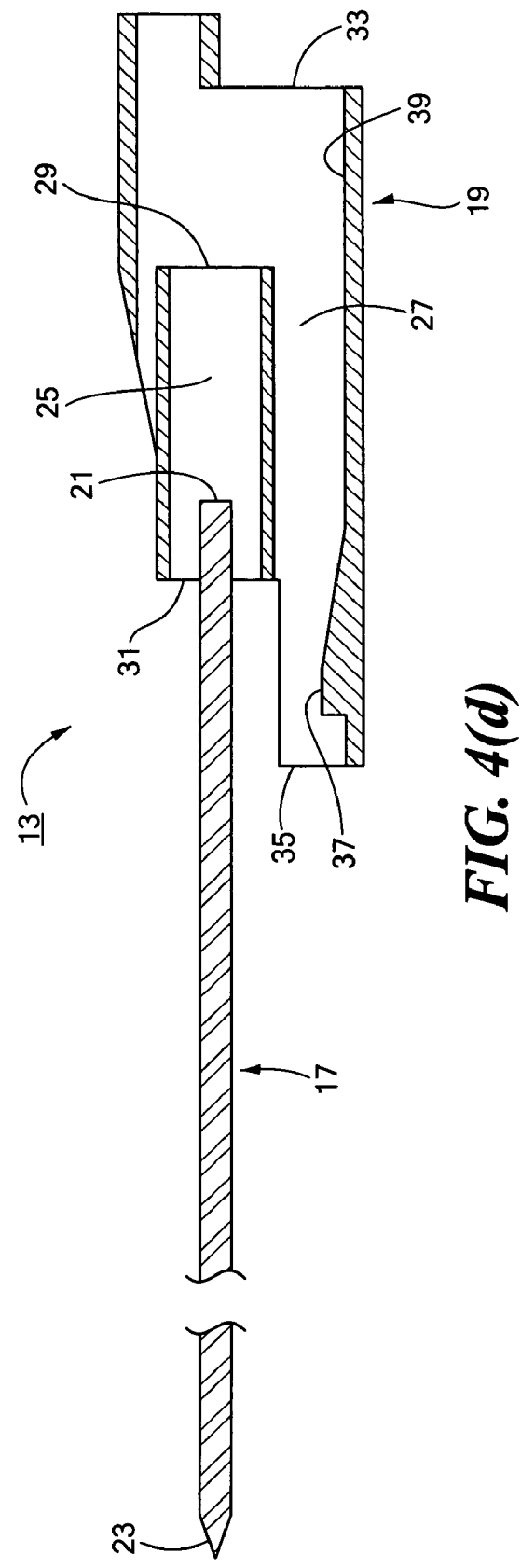

Referring now to FIGS. 1 through 3, there are shown perspective, top and section views, respectively, of one embodiment of an access needle constructed according to the teachings of the present invention, said access needle being represented generally by reference numeral 11. As will be discussed further below, access needle 11 may be used, for example, in a percutaneous endoscopic jejunostomy (PEJ) procedure.

Access needle 11 comprises a stylet assembly 13, a safety sheath assembly 15 and a cannula assembly 16.

Stylet assembly 13, which is also shown separately in FIGS. 4(a) through 4(d), comprises a stylet 17 and a stylet hub 19. Stylet 17, which is preferably made of stainless steel, is a solid, generally cylindrical member of small diameter. Stylet 17 includes a proximal end 21 and a distal end 23, distal end 23 being in the shape of a sharp, three-sided tip adapted to penetrate one or more body parts, such as the abdomen and jejunum of a patient undergoing a percutaneous endoscopic jejunostomy procedure.

Stylet hub 19, which is preferably made of molded plastic, is shaped to include a first chamber 25 and a second chamber 27. First chamber 25 is generally tubular and has an open proximal end 29 and an open distal end 31. Proximal end 21 of stylet 17 is fixedly disposed within first chamber 25 (by means of an adhesive bead 26 applied to a side of stylet 17), with the remainder of stylet 17 extending distally through open distal end 31 of first chamber 25. Second chamber 27 coaxially surrounds much of first chamber 25 and has an open proximal end 33 and an open distal end 35. A detent 37 is provided on a bottom wall 39 of hub 19, detent 37 being spaced proximally a short distance from distal end 35.

Safety sheath assembly 15, which is also shown separately in FIGS. 5(a) and 5(b), includes a sheath 41 and a shuttle 43. Sheath 41, which is preferably made of stainless steel, is a generally tubular member having a proximal end 45 and a distal end 47. For reasons to be discussed below, sheath 41 is appropriately dimensioned to coaxially receive stylet 17. A longitudinal slit 49 is provided in sheath 41 to avoid contacting bead 26.

Shuttle 43, which is preferably made of molded plastic, is shaped to include a first arm 51, a second arm 53, and a connecting member 55. First arm 51, which is positioned within first chamber 25 of stylet hub 19 and is adapted for sliding movement back and forth within chamber 25, has a proximal end 57 and a distal end 59, distal end 59 of first arm 51 being mounted coaxially around proximal end 45 of sheath 41. Second arm 53, which is positioned on top of bottom wall 39 of stylet hub 19 and is adapted for sliding movement back and forth along wall 39, is biased away from first arm 51 and has a proximal end 61 and a distal end 63. A transverse slot 65 is provided in second arm 53 just in front of distal end 63, slot 65 being appropriately dimensioned to receive the distal end of detent 37 once distal end 63 has been moved distally beyond detent 37. Second arm 53 is also shaped to include a pair of upwardly-extending pawls 67-1 and 67-2, the purpose of pawls 67-1 and 67-2 to be discussed below.

Figure 6A:
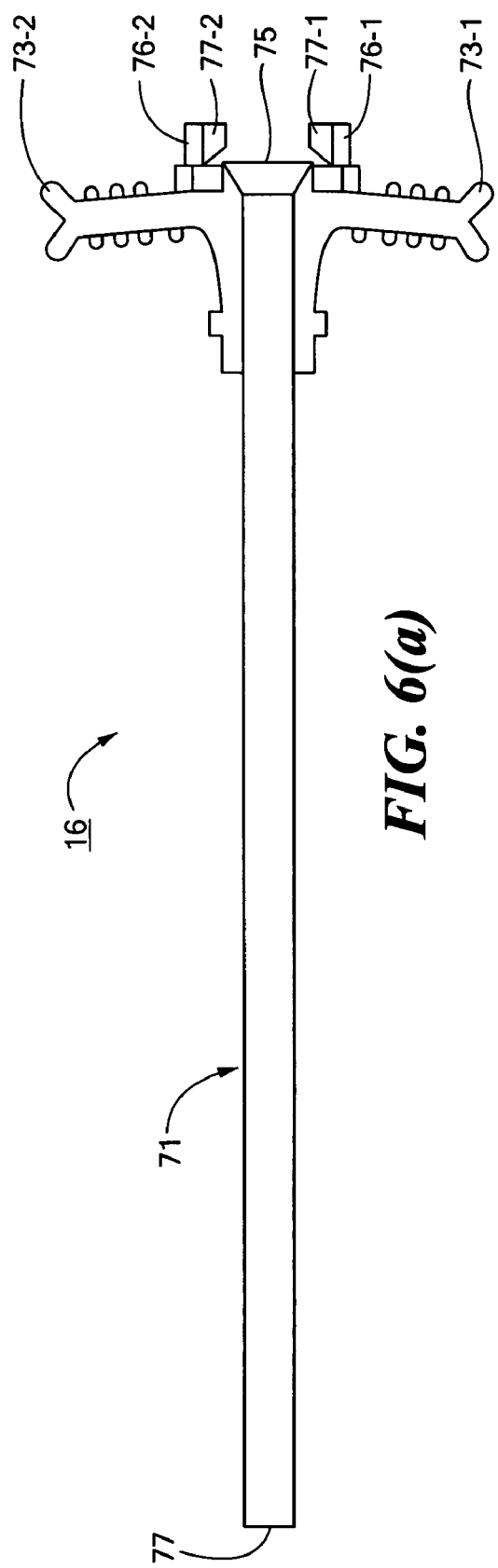
FIGS. 6(a) and 6(b) are top and side views, respectively, of the cannula assembly of the access needle of FIG. 1.
Figure 6B:
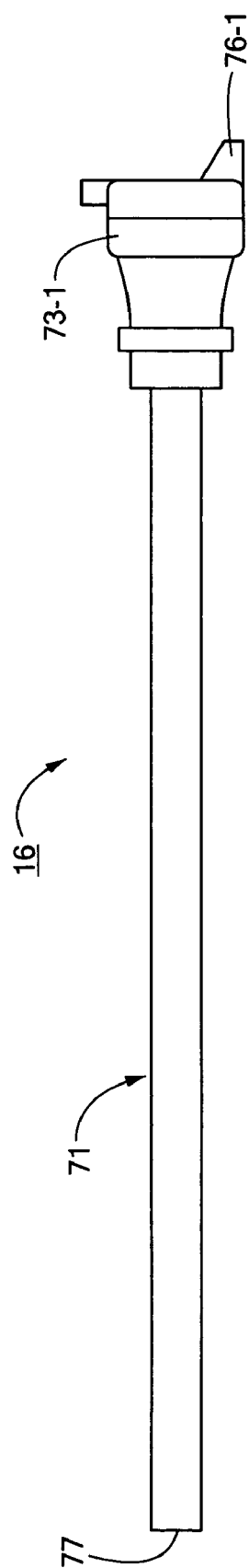

Cannula assembly 16, which is also shown separately in FIGS. 6(a) and 6(b), comprises a cannula 71 and a pair of cannula brackets 73-1 and 73-2, cannula brackets 73-1 and 73-2 being fixed to cannula 71 and jointly defining a cannula hub. Cannula 71, which may be made of a suitable metal or molded plastic, is a tubular member having a proximal end 75 and a distal end 77, proximal end 75 being outwardly flared. Cannula 71 is appropriately dimensioned to coaxially receive sheath 41 and stylet 17 in the manner to be discussed below. As can be seen in FIGS. 1 through 3, the distal ends of stylet 17 and sheath 41 extend about 1.5 inch beyond distal end 77 of cannula 71.

Brackets 73-1 and 73-2, which may be made of molded plastic, are shaped to include generally L-shaped tabs 76-1 and 76-2, respectively. Tabs 76-1 and 76-2 include ramped portions 77-1 and 77-2, respectively, ramped portions 77-1 and 77-2 detachably engaging pawls 67-1 and 67-2, respectively, of shuttle 43 in the manner to be described below.

To use access needle 11, for example, to create an access port through the abdominal and jejunal walls of a patient as part of a percutaneous endoscopic jejunostomy (PEJ) procedure, one begins with access needle 11 in the state shown in FIGS. 1 through 3, with shuttle 43 in its most proximal position relative to hub 19 and distal end 23 of stylet 17 extending beyond distal end 47 of sheath 41 such that only the tip of stylet 17 is exposed. After properly anesthetizing the patient and using an endoscope transorally placed in the jejunum to transilluminate a desired insertion site, an operator inserts the distal ends of stylet 17 and sheath 41, but not cannula 71, through the abdominal and jejunal walls of the patient until they are visible to the endoscope through an observation channel therein. A snare, which is inserted into the jejunum through a snare channel of the endoscope, is then used to securely capture the inserted end of stylet 17. With stylet 17 thus captured by the snare, stylet 17 is pulled proximally so as to engage the wall of the jejunum. Further pulling of stylet 17 results in the jejunum being held stationary against the abdominal wall.

Figure 7:
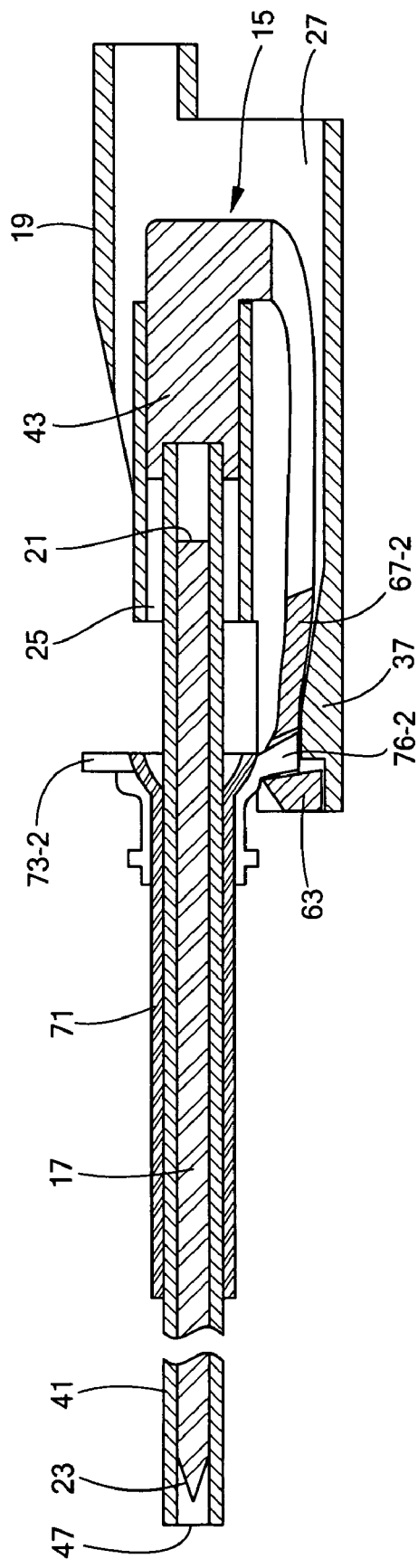
FIG. 7 is a section view of the access needle of FIG. 1, with the shuttle moved to its most distal position by the cannula assembly, the sheath shielding the distal end of the stylet.

With the jejunum thus held stationary against the abdominal wall by the snare and stylet 17, cannula 71 is then moved distally relative to stylet 17 until it penetrates the jejunum through the opening previously created by stylet 17. As can be seen in FIG. 7, due to the engagement of tabs 76 with pawls 67, the distal movement of cannula 71 relative to stylet 17 causes shuttle 43 to be moved distally until distal end 63 of shuttle 43 is moved past detent 37, causing distal end 63 of shuttle 43 to spring into the space between detent 37 and distal end 35 of stylet hub 19 and causing the distal end of detent 37 to be lockingly received in slot 65 of shuttle 43 (thereby precluding any further distal movement of shuttle 43). Such distal movement of shuttle 43, in turn, causes sheath 41 to be moved distally, whereby sheath 41 shields distal end 23 of stylet 17. As seen in FIGS. 8(a) and 8(b), continued distal movement of cannula 71 relative to stylet 17 causes tabs 76-1 and 76-2 to disengage from pawls 67-1 and 67-2, respectively.

With distal end 77 of cannula 71 thus inserted into the jejunum, the snare is loosened slightly from stylet 17 and is then moved from stylet 17 to the inserted portion of cannula 71. The snare is then tightened around the inserted portion of cannula 71. Stylet assembly 13 and safety sheath assembly 15 are then completely removed from cannula 71. Cannula 71 may now be used in the conventional manner to receive a suture or guidewire of the type used to implant a PEJ device in the patient.

Figure 9:
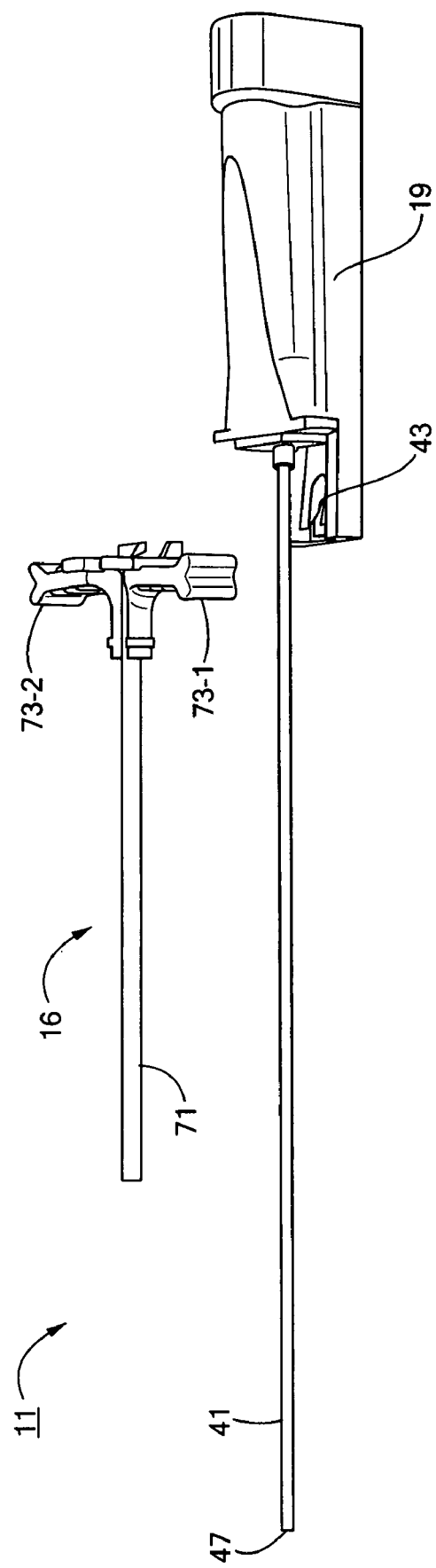
FIG. 9 is a perspective view of the access needle of FIG. 1, with the cannula assembly completely removed from the stylet assembly and the safety sheath assembly.

As can be seen in FIG. 9, when cannula assembly 16 is completely removed from the combination of stylet assembly 13 and safety sheath assembly 15, distal end 23 of stylet 17 is automatically shielded by sheath 41, thereby preventing inadvertent needle sticks with stylet 17. Moreover, because shuttle 43 cannot easily be moved proximally relative to stylet assembly 13 without first re-attaching tabs 76-1 and 76-2 to pawls 67-1 and 67-2, respectively, there is little risk of distal end 23 of stylet 17 becoming inadvertently exposed.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. An access needle, said access needle comprising:
   (a) a stylet, said stylet having a proximal end and a sharpened distal end;
   (b) a stylet hub, said proximal end of said stylet being fixedly coupled to said stylet hub, said stylet hub including a first chamber and a second chamber, said second chamber surrounding at least a portion of said first chamber and extending generally parallel thereto, said stylet hub comprising a detent;
   (c) a sheath coaxially surrounding said stylet, said sheath having a proximal end and a blunt distal end;
   (d) a shuttle, said shuttle being coupled to said proximal end of said sheath, said shuttle being movable between a first position in which said sharpened distal end of said stylet is exposed and a second position in which said sharpened distal end of said stylet is shielded by said blunt distal end of said sheath, said shuttle including means for releasably engaging said detent; and
   (e) a cannula, said cannula having a proximal end and a distal end, said sheath being removably coaxially received in said cannula, said cannula having a shuttle engagement structure for engaging the shuttle,
   wherein in the first position, the cannula is engaged with the shuttle by the shuttle engagement structure; and
   wherein distal movement of the cannula relative to the stylet causes distal movement of the shuttle until the second position is reached, wherein in the second position the detent of the stylet hub is engaged with the shuttle and continued distal movement of the cannula causes disengagement of the cannula from the shuttle.

2. The access needle of claim 1, wherein said stylet is a solid member.

3. The access needle of claim 1, wherein said distal end of said stylet extends about 1.5 inches beyond said distal end of said cannula.

4. The access needle as claimed in claim 1 wherein said proximal end of said stylet is mounted within said first chamber.

5. The access needle as claimed in claim 4 wherein said shuttle includes a first arm and a second arm, said proximal end of said sheath being mounted in said first arm, said first arm being slidably disposed within said first chamber.

6. The access needle as claimed in claim 5 wherein said second arm of said shuttle is slidably disposed within said second chamber of said stylet hub.

7. The access needle as claimed in claim 6 wherein said second arm of said shuttle includes said means for releasably engaging said detent.

8. The access needle as claimed in claim 7 further comprising a cannula hub, said cannula hub being mounted on said proximal end of said cannula, said cannula hub having the shuttle engagement structure.

9. The access needle as claimed in claim 8 wherein said shuttle is shaped to include a pair of pawls and wherein said releasably engaging means of said cannula hub includes a pair of tabs releasably engageable with said pawls.

10. The access needle as claimed in claim 1 wherein said shuttle is lockable in said second position.

11. The access needle of claim 1 wherein said stylet is a solid member.

12. The access needle of claim 1, wherein said distal end of said stylet extends about 1.5 inches beyond said distal end of said cannula.

13. The access needle of claim 1, wherein in the first position, the cannula is directly engaged with the shuttle by the shuttle engagement structure.

14. An access needle comprising:
   (a) a stylet assembly, said stylet assembly comprising a stylet and a stylet hub, said stylet having a proximal end and a sharpened distal end, said proximal end being fixedly mounted within said stylet hub, said stylet hub comprising a detent;
   (b) a safety sheath assembly, said safety sheath assembly comprising a sheath and a shuttle, said sheath coaxially receiving said stylet and having a proximal end and a blunt distal end, said shuttle being slidably mounted in said stylet hub and having a complete range of motion between a first position in which said sharpened distal end of said stylet is exposed and a second position in which said sharpened distal end of said stylet is shielded by said blunt distal end of said sheath, said shuttle comprising a slot for releasably engaging said detent; and (c) a cannula, said cannula having a proximal end a distal end, said sheath being removably coaxially received in said cannula, said cannula having a shuttle engagement structure for engaging the shuttle, wherein in the first position, the cannula is engaged with the shuttle by the shuttle engagement structure; and wherein distal movement of the cannula relative to the stylet causes distal movement of the shuttle until the second position is reached, wherein in the second position the detent of the stylet hub is engaged with the shuttle and continued distal movement of the cannula causes disengagement of the cannula from the shuttle.

15. The access needle of claim 14 wherein said shuttle is lockable in said most distal position.

16. The access needle as claimed in claim 14 further comprising a cannula hub, said cannula hub being mounted on said proximal end of said cannula, said cannula hub having the shuttle engagement structure.

17. The access needle as claimed in claim 14 wherein the stylet hub includes a first chamber and a second chamber, said proximal end of said stylet being disposed in said first chamber, said shuttle comprising an arm slidably mounted in said second chamber.

18. The access needle of claim 14, wherein in the first position, the cannula is directly engaged with the shuttle by the shuttle engagement structure.

19. An access needle comprising:
(a) a stylet, said stylet having a proximal end and a sharpened distal end;
(b) a stylet hub, said stylet hub comprising a first chamber and a second chamber, said first chamber having an open proximal end and an open distal end, the proximal end of said stylet being fixedly mounted within said first chamber, said second chamber surrounding at least a portion of said first chamber and extending generally parallel thereto, wherein a detent is provided within said second chamber;
(c) a sheath coaxially surrounding said stylet, said sheath having a proximal end and a blunt distal end;
(d) a shuttle, said shuttle being coupled to said proximal end of said sheath, said shuttle being movable between a first position in which said sharpened distal end of said stylet is exposed and a second position in which said sharpened distal end of said stylet is shielded by said blunt distal end of said sheath, said shuttle including a first arm and a second arm, said first arm being slidably mounted within said first chamber of said stylet hub, said second arm being disposed within said second chamber of said stylet hub, said second arm comprising a transverse slot for releasably engaging said detent, said second arm further comprising a pair of recesses;
(e) a cannula, said cannula having a proximal end and a distal end, said sheath being removably coaxially received in said cannula; and
(f) a cannula hub, said cannula hub being coupled to said proximal end of said cannula, said cannula hub comprising a pair of tabs, said tabs being insertable into said recesses of said shuttle to detachably couple said cannula hub to said shuttle, wherein in a first position, the tabs of the cannula hub are received in said recesses of the shuttle to directly couple the cannula to the shuttle; and wherein distal movement of the cannula relative to the stylet causes distal movement of the shuttle until the shuttle reaches a second position in which the transverse slot of the shuttle engages the detent of the stylet hub.

* * * * *